United States Patent [19]

Baldwin et al.

[11] 4,147,699
[45] Apr. 3, 1979

[54] α-LACTAM PRECURSORS OF PENICILLIN AND CEPHALOSPORIN ANTIBIOTICS

[75] Inventors: Jack E. Baldwin, Boston; Andrew T. Au, Somerville, both of Mass.

[73] Assignee: Massachusetts Institute of Technology, Cambridge, Mass.

[21] Appl. No.: 865,638

[22] Filed: Dec. 29, 1977

Related U.S. Application Data

[63] Continuation of Ser. No. 741,313, Nov. 11, 1976, abandoned, which is a continuation of Ser. No. 567,046, Apr. 10, 1975, abandoned.

[51] Int. Cl.$^2$ ............................................. C07D 275/04
[52] U.S. Cl. ........................ 260/306.7 C; 260/239.1; 424/246
[58] Field of Search ................................ 260/306.7 C

[56] References Cited

U.S. PATENT DOCUMENTS

| 3,799,938 | 3/1974 | Seusler et al. | 260/306.7 |
| 3,862,164 | 1/1975 | Cooper | 260/306.7 |
| 3,900,487 | 8/1975 | Underwood et al. | 260/306.7 |

Primary Examiner—Nicholas S. Rizzo
Attorney, Agent, or Firm—Arthur A. Smith, Jr.; Paul J. Cook

[57] ABSTRACT

This invention provides novel α-lactam precursors of known and novel microbiologically active penicillins and cephalosporins and to a process for making the α-lactam precursors from a L-cysteinylvaline dipeptide or a polypeptide containing the L-cysteine with other amino acids. The α-lactam precursors are represented by the Formula I.

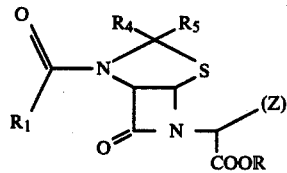

Formula I wherein Z is

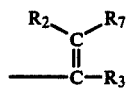

Formula A

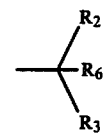

Formula B or

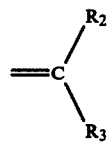

Formula C and wherein R, $R_1$, $R_2$, $R_3$, $R_4$, $R_5$, $R_6$ and $R_7$ are defined herein. When Z has the structure of Formula A, the α-lactam is a precursor for cephalosporins. When Z has the structure of either Formula B or Formula C, the α-lactam is a precursor for a penicillin.

4 Claims, No Drawings

α-LACTAM PRECURSORS OF PENICILLIN AND CEPHALOSPORIN ANTIBIOTICS

The Government has rights in this invention pursuant to Grant No. NIH-R01-AI1197-01 awarded by the Department of Health, Education and Welfare.

BACKGROUND OF THE INVENTION

This is a continuation, of application Ser. No. 741,313 filed Nov. 11, 1976, now abandoned; which is a continuation of Ser. No. 567,046 filed Apr. 10, 1975 now abandoned. The invention herein described was made in the course of work performed under a grant from the National Institute of Health.

Prior to the present invention, there has been no known completely biosynthetic route to produce penicillins or cephalosporins. At the present time, all penicillins and cephalosporins are formed from fungi, chiefly *Penicillum chrysogenum* or *cephalosporium sp.* and recovered as a natural product. It has been hypothesized that polypeptides, particularly polypeptides including in their structure the amino acids, L-cysteine and valine are precursors to the penicillins or cephalosporins. However, the experimental work conducted thus far to verify these hypotheses has failed to establish this fact with the necessary degree of assurity.

It would be highly desirable to provide a process for the complete biosynthesis of penicillins and cephalosporins from readily available starting materials rather than relying upon fungi to produce the natural penicillins and cephalosporins. This is because the structural variation that can be made upon the natural penicillins and cephalosporins is quite limited because of the relative fragility of their structure. Thus, at the present time, a great effort must be made during the synthesis of modified penicillins and cephalosporins to protect a given portion of the chemical structure against the reaction conditions needed to modify another portion of the chemical structure. This requires undesirable additional reaction and separation steps to attain the modified penicillin and cephalosporin. If a complete biosynthetic type process were available it would be possible to form a direct precursor to the desired penicillin having the desired substitution prior to forming the 7-oxo-4-thia-1-azabicyclo [3.2.0] heptane ring.

SUMMARY OF THE INVENTION

This invention provides novel β-lactam precursors for penicillins represented by Formula I.

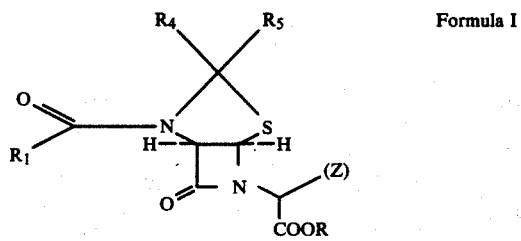

Formula I wherein Z is

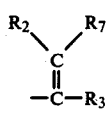

Formula A

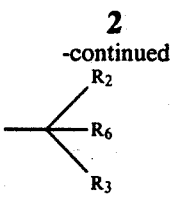

Formula B

Formula C and wherein R, $R_1$, $R_2$, $R_3$, $R_4$, $R_5$, $R_6$ and $R_7$ are defined herein. When Z has the structure of Formula A, the β-lactam is a precursor for cephalosporins. When Z has the structure of either Formula B or Formula C, the β-lactam is a precursor for a penicillin. The compounds of this invention are produced from polypeptides containing in its structure, the condensation product of L-cysteine, particularly a tripeptide containing a L-cysteinylvaline dipeptide. The L-cysteine moiety is first protected by forming the thiazolidine ring. Thereafter, the ring carbon $CH_2$ adjacent to the sulfur atom is activated by reaction with a diacylperoxide, a diaroylperoxide, an aroylperoxy ester or an acylperoxy ester, followed by ring closure to form the β-lactam compounds of this invention.

These compounds can be easily modified since both the sulfur atom and the nitrogen atom in the thiazolidine ring are protected. After the β-lactam has the desired structure, the corresponding penicillin structure is formed by ring formation. For example, ring formation to the corresponding penicillin structure can be effected with the compound of Formula I wherein $R_2$ and $R_3$ are alkyl, $R_6$ is hydroxyl, $R_1$ is trichloroethoxy, $R_4$ and $R_5$ are methyl and R is nitrobenzyl by reacting it with zinc dust in acetic acid or formic acid to give the compound of Formula VIII.

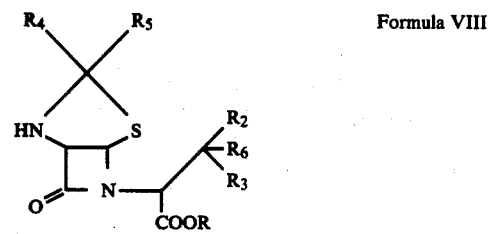

Formula VIII

The compound of Formula VIII then is reacted with a strong acid such as hydrochloric acid in an inert solvent such as dichloromethane to give the cyclized penicillin of Formula IX.

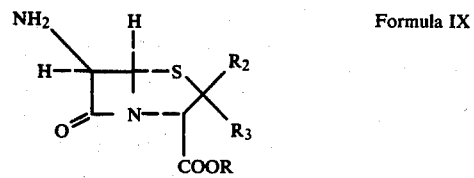

Formula IX which can then be deprotected by catalytic hydrogenation to the acid form wherein R is hydrogen and $R_2$ and $R_3$ are alkyl.

The process of this invention is illustrated by the following reaction scheme:

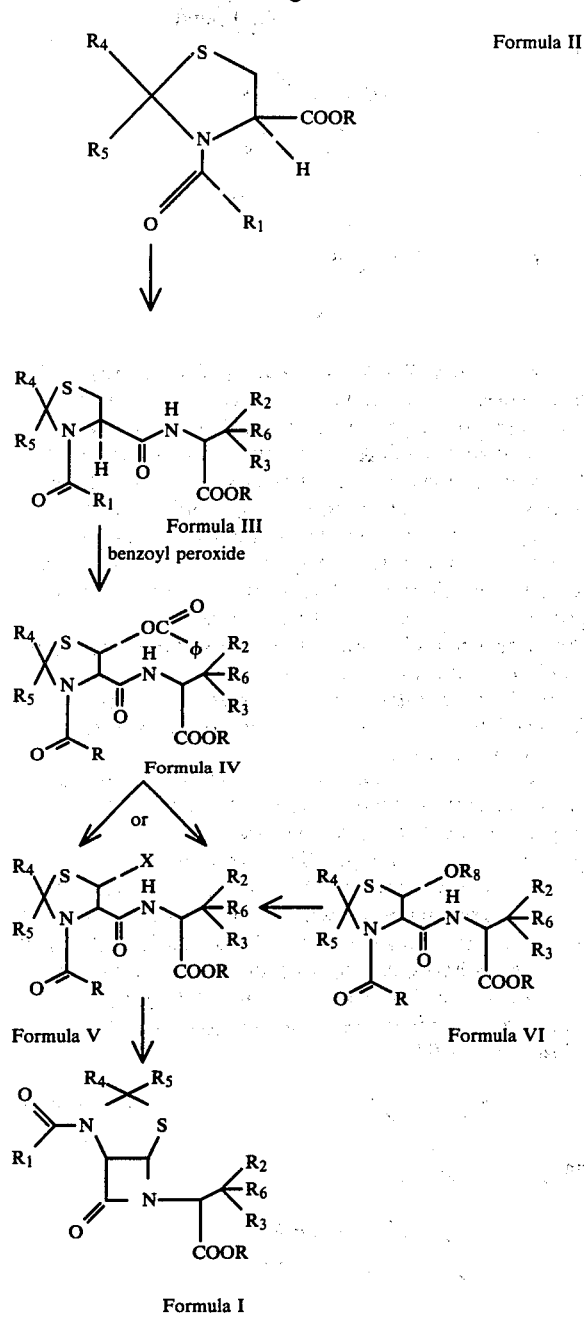

Formula II

Formula III benzoyl peroxide

Formula IV

Formula V      Formula VI

Formula I

The process of this invention is based upon the discovery that the dipeptide of L-cysteine and a second amino acid which can be converted to a β-lactam compound by first activating the ring carbon atom to the sulfur atom in the L-cysteine, substituting a chloride, bromide, iodide, an arylsulfonate group or an alkylsulfonate group on the activated carbon atom and forming the β-lactam ring by a cyclization reaction while evolving halide, an alkylsulfonate or an arylsulfonate.

The starting dipeptide or polypeptide can be derived from any source so long as the cysteine is of the L-configuration. A tripeptide containing L-cysteine and valine suitable as a starting material is obtained by well known procedures. Alternatively, the dipeptide can be obtain by protecting the reactive sulfur and nitrogen sites of the L-cysteine molecule such as by reacting L-cysteine with a ketone such as acetone to form the compound of Formula II wherein $R_4$ and $R_5$ are alkyl to provide the compound of Formula II. The protected L-cysteine and the nitrogen is protected by acylation wherein $R_1$ = alkyl, aryl or various alkoxy groups, then is reacted with a suitable amino acid which produces the dipeptide of Formula III by well known condensation reactions. Representative amino acids which can be condensed with L-cysteine to form the dipeptide include β-hydroxy valine, β - alkoxyvaline, 2-amino-3-methyl-3-butenoic acid and vinyl glycine. The hydrogen atom of the carboxylic acid group of the second amino acid is replaced with any suitable acid protecting group by any well known procedure so that the dipeptide can be reacted further in accordance with this invention. It is to be understood that the sulfur and nitrogen atoms of the L-cysteine need not be protected prior to reaction with valine or other amino acid. The dipeptide or polypeptide can be formed first by condensing the amino acids and thereafter the sulfur and nitrogen atom can be protected by the manner described above.

The peptide of Formula III then is reacted to activate the ring carbon atom of the L-cysteine residue such that the carbon atom can be substituted subsequently with chloride, bromide, iodide, alkylsulfonate, arylsulfonate, alkoxy or hydroxide. Suitable organic peroxide activating agents include diaroylperoxides such as benzoyl peroxide, p-nitrobenzoyl peroxide or the like as well as diacylperoxides such as diacetyl peroxide or the like, aroylperoxy esters of the formula, Ar—CO—O—O—R or acylperoxy esters of the formula, Alkyl—CO—O—O—R wherein Ar is phenyl or substituted phenyl and R is lower alkyl including methyl, ethyl, butyl, propyl, hexyl or the like. For convenience the reaction will be described herein with reference to the use of benzoyl peroxide. It is to be understood that the reaction also can be carried out successfully with other activating agents set forth. The reaction is carried out in the absence of free oxygen in an inert atmosphere such as nitrogen and in an inert solvent such as carbon tetrachloride, bromotrichloromethane, chloroform or ethylene dichloride at elevated temperatures, usually within the range of about 25° C. to 100° C., preferably 65° C. to 75° C. It is desirable to employ a stoichiometric excess of the peroxide to assure relatively complete reaction. The product represented by Formula IV is recovered as white crystals by filtration. The filtrate also can be concentrated to recover additional quantities of the product. The benzoyloxylation is highly stereo-specific and the desired sterochemistry can be confirmed easily by the pyrolytic elimination of benzoic acid and also by the proton magnetic resonance spectrum.

The conversion of the compound of Formula IV to the compound of Formula V can be effected by either of two routes. The preferred route is a direct route wherein the compund of Formula IV is reacted with a nonaqueous solution of hydrogen chloride, hydrogen bromide or hydrogen iodide or an alkylsulfonyl halide or an arylsulfonyl halide in an inert solvent such as chloroform, carbon tetrachloride or dichloromethane. In any event, this reaction is conducted under anhydrous conditions. The reaction is conducted at a temperature between about −25° C. and 25° C., preferably about 0° C. At temperatures below about −25° C., the reaction is undesirably slow while at temperatures above about 25° C., the reaction is less clean. The halogenated product, alkylsulfonated product or arylsulfonated product is recovered by evaporation of the solvent.

While employing the alternative route to the compound of Formula V, the hydroxylated or alkoxylated compound of Formula VI wherein $R_8$ is hydrogen or $C_1$-$C_7$ alkyl first is produced by hydrolyzing the compound of Formula IV with an aqueous ether mixture such as dioxane or ethylene glycol or alkoxylating the compound with a lower alkanol such as methanol, propanol or the like. The hydrolysis or alkoxylation is conducted in a sealed container at an elevated pressure greater than about 15 psi and at a temperature between about 100° C. and about 150° C. The product obtained by removal of solvent at less than 25° C. is a crystalline material and is somewhat unstable at room temperature. Thereafter, the product is dissolved in an inert solvent such as set forth above and is maintained at a temperature below about 25° C., preferably below 0° C.

The hydroxylated or alkoxylated product is converted to the halogenated, alkysulfonated or arylsulfonated product of Formula V by reacting it with a halide donor in the presence of weak base in an inert solvent. Preferred halide donors include alkylsulfonyl chlorides, bromides or iodides such as methanesulfonyl chloride, methanesulfonyl bromide, ethanesulfonyl chloride, ethanesulfonyl bromide or equivalent arylsulfonyl chlorides, bromides or iodides such as phenylsulfonyl chloride, toluenesulfonyl bromide or the like. Other halide donors include hydrogen chloride, hydrogen bromide or hydrogen iodide. When this reaction is carried out at relatively low temperatures within the temperature range set forth above, the product will be substituted with alkysulfonate or arylsulfonate admixed with the halogen-substituted compound. When conducting the reaction within the higher temperature range, the halogenated product will predominate over the arylsulfonated or alkysulfonated product. In any event, all the derivatives can be cyclized subsequent to the β-lactam product of this invention. Representative weak bases are trialkylamines such as triethylamine or dimethylaniline or cyclic amines including pyridine. Exemplary inert solvents are methylene chloride, chloroform or dichloroethylene. The reaction is conducted at a temperature between about −25° C. and 0° C. to assure relatively high yields of the halogenated, alkysulfonated or arylsulfonated product. The product is recovered by any suitable means such as by evaporation and washing with water to remove excess amine and acids.

Ring closure of the compound of Formula V to form the β-lactam of Formula I is effected in the presence of a strong base in an aprotic medium. Suitable bases include alkali metal hydrides such as sodium hydride, or potassium hydride or alkali metal alkoxides such as potassium t-butoxide. Suitable aprotic materials include dimethylformamide, dimethyl sulfoxide or dichloromethane. Alternatively, the reaction with the base can be conducted in an inert solvent with a tetra-N-alkylammonium salt. Suitable inert solvents include those solvents set forth above. Suitable salts include tetra-N-butylammonium iodide, tetra-N-ethylammonium iodide or tetra-N-ethylammonium bromide. The reaction is conducted at a temperature between about 0° C. and 40° C., preferably about 25° C.

In the formulae set forth above, R is a carboxyl protective organic group such as $C_1$-$C_4$ alkyl, benzyl, diphenylmethyl, 4-methoxy-diphenylmethyl, 3,5-dimethoxybenzyl, 4-methoxybenzyl, 4-nitrobenzyl or the like.

$R_1$ is $C_1$-$C_7$ alkyl, phenyl, substituted phenyl including halophenyl, lower alkylphenyl, lower alkoxyphenyl, hydroxyphenyl, alkylthiomethyl, 5'-protected amino-5'-carboxyvaleramido or 5'amino-5'-carboxyvaleramido, carboaryloxy such as carbobenzyloxy, carboalkoxy such as carbotrichloroethyloxy; trifluoroacetyl or the like.

$R_2$ and $R_3$ are hydrogen, $C_1$ to $C_4$ alkyl or $C_1$ to $C_4$ alkoxy, $R_4$ and $R_5$ are $C_1$ to $C_4$ alkyl, X is chloride, bromide, iodide, alkysulfonyl or arylsulfonyl, $R_6$ is hydrogen hydroxyl or an ester derivative of hydroxyl such as acyloxy, benzoxyloxy or alkoxy or halide, $R_7$ is hydrogen, $C_1C_4$ alkyl or $C_1$-$C_4$ alkoxy.

The following examples illustrate the present invention and are not intended to limit the same.

EXAMPLE I

This example illustrates the step of activating the ring carbon atom α to the sulfur atom in the thiazolidine ring with benzoyl peroxide. Under a nitrogen atmosphere, 1.5 grams of the dipeptide having the formula:

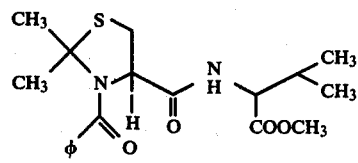

was mixed with 3.2 grams of benzoyl peroxide in carbon tetrachloride (30ml) and maintained at 70° C. for 90 minutes. The mixture was cooled to room temperature and the carbon tetrachloride was removed in vacuo. After removing the carbon tetrachloride, 50 ml acetone, 1 ml acetic acid, 5 ml water and 5.5 grams potassium iodide were added to the residue and stirred for 30 minutes at room temperature. The mixture was concentrated again by heating at about 25° C. and ethyl acetate was then added to effect extraction. The extract was washed with sodium bisulfite and sodium bicarbonate solution, dried over magnesium sulfate and concentrated to form crystals which were separated by filtration to give a yield of 0.75 grams and was washed with a small amount of carbon tetrachloride. The filtrate was concentrated and the oil obtained was chromatographed through a silica gel and another 0.75 grams of the products (m.p. 193°–194° C.) was obtained. The product, as confirmed by spectral data had the following formula:

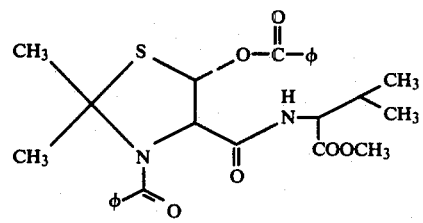

EXAMPLE II

This example illustrates the conversion of the product of Example I to the hydroxy-substituted intermediate having the formula:

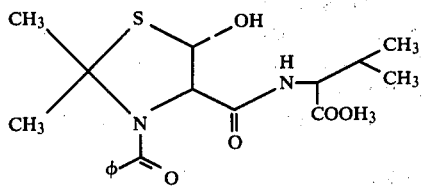

In a sealed test tube, 125 mg of the benzoate in 10 ml of 70% aqueous dioxane was dept at 125° C. for 5 hours. After cooling to room temperature, the material was extracted with ethyl acetate and the extract was dried over magnesium sulfate and concentrated to an oil. This oil was purified in a column of Florasil and 55 mg. of white crystals was obtained. Since the concentrated product decomposes very easily at room temperature, the work-up should be done at 0° C. All spectral data show the compound to have the formula set forth in this example.

EXAMPLE III

This example illustrates the conversion of the compound obtained by way of Example II to the compound of the formula:

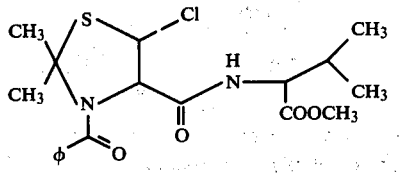

The product obtained by way of Example II was dissolved in dichloromethane and 40 drops of triethylamine at 0° C. The resultant composition then was admixed with 15 drops of methanesulfonyl chloride and stored in a freezer at −5° C. overnight. The resultant composition was added to ice, diluted with ether, washed with cold dilute hydrochloric acid, saturated sodium bicarbonate solution, dried, and concentrated to a liquid. Upon addition of anhydrous ether in the composition, crystallization occurred to form a white solid having a melting point between 136.5° C. and 138° C. Analysis of the product by nuclear magnetic resonance confirmed the structure set forth above in this example.

EXAMPLE IV

This example illustrates the formation of the product of Example III directly from the product of Example I.

At 0° C., 30 ml of CH₂Cl₂ was saturated with HCl then 500 ml. of the benzoate was added and stirred for 1.5 hours. The mixture was poured into ice and ethyl acetate. The extract was recovered and washed with water and saturated NaHCO₃ and NaCl. Thereafter, it was dried and concentrated to a solid, 405 mg. having a melting point of 136° C. −137.5° C.

EXAMPLE V

This example illustrates the conversion of the product of Example IV to the β-lactam of the formula:

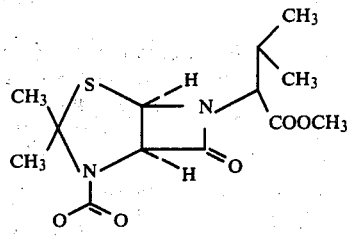

Under a nitrogen atmosphere, 6 mg. of the 57% NaH was added to a mixture containing 27 mg. of the product from Example IV, a catalytic amount of tetra-N-butylammonium iodide (about 1mg.) in 10 ml of dry dichloromethane. The reaction is carried out at room temperature (about 25° C.) and, after 1.5 hours, more dichloromethane was added, followed by washing with dilute HCl, saturated NaHCO₃ and saturated NaCl. The composition then was concentrated to an oil, which was mainly one product, purified by chromatography. Analysis of the product by nuclear magnetic resonance confirmed the structure set forth above in this example.

EXAMPLE VI

This example illustrates the formation of the compound of the formula:

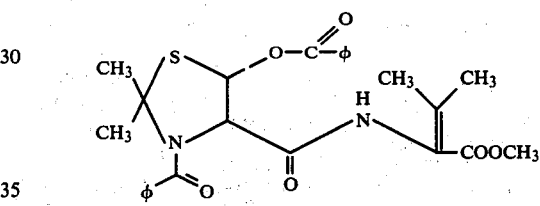

from the dipeptide of the formula:

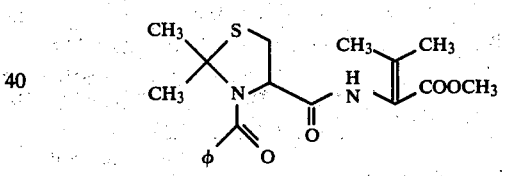

100 mg. of the dipeptide (0.266 mole) and 163 mg. (2.5 eq.) benzoyl peroxide were suspended in 3 ml. carbon tetrachloride and placed in an oil bath preheated to 70° C. under a nitrogen atmosphere and a condenser. Heating was continued for 1.5 hours and then was cooled to room temperature and stirred for 10 minutes. Thereafter, 47 μl of trimethyl phosphite (0.0496 grams) was added to the composition and stirring was conducted at room temperature for 30 minutes and a yellow oil was formed thereby. The mixture was dissolved in 5.0 ml. of pyridine and 0.5 ml water and heated in a steam bath for 40 minutes and thereafter it was heated to evaporation to leave a brown oil. The brown oil was dissolved in trichloromethane and this solution was washed twice with 25 ml water, four times with 25 ml NaCl, three times with 25 ml saturated NaHCO₃ and twice with 25 ml saturated NaCl. This product then was dried with MgSO₄ above then was left in a freezer overnight. Crystal formation occurred and the crystalline product (110 mg, 82.5% yield) was recovered by filtration and then washed in CCl₄. After repeated CCl₄ washings, the crystals remained light tan. This product can be converted to the corresponding β-lactam by the procedures set forth in the aboxe example.

EXAMPLE VII

This example illustrates a procedure for making the compound of the formula:

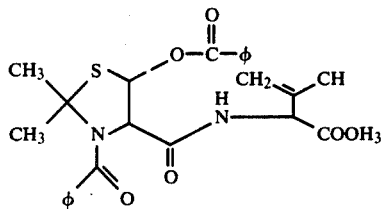

The thiazolidine dipeptide comprising the condensation product of L-cysteine and 2-amino-3-methyl-3-butenoic acid (1.76 grams, 4.65 mmoles) and benzoyl peroxide (2.8 grams, 2.5 equivalents) were suspended in 60 ml. of $CCl_4$ under a nitrogen atmosphere and then placed in an oil bath at 73° C. After 1.5 hours, the reaction mixture was cooled to room temperature and the composition was then heated to effect evaporation to dryness. A small amount of $CCl_4$ was added to the residue and the resultant composition was refrigerated. The product was filtered to recover 818 mg of substance having a melting point of 104°–105° C. identified as benzoyl peroxide. The remaining yellow oil was dissolved in ethyl acetate, was washed three times with 25 ml saturated aqueous sodium chloride, dried and evaporated to recover 926 mg. product. This product can be converted to the corresponding $\beta$-lactam by the procedures set forth in the above examples.

What is claimed is:

1. A $\beta$-lactam of the formula

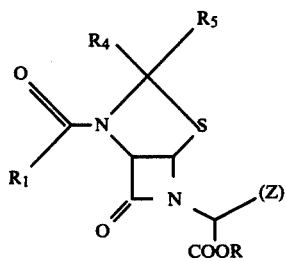

wherein R is a carboxyl protective organic group, $R_1$ is $C_1$–$C_7$ alkyl, phenyl, halophenyl lower alkylphenyl, lower alkoxyphenyl, hydroxyphenyl, 5'amino-5'carboxyvaleramido, 5'-protected amino-5'-carboxyvaleramido, carbobenzyloxy, carbotrichloroethyloxy or trifluoroacetyl, Z has a formula selected from the group consisting of:

 Formula A

 Formula B and

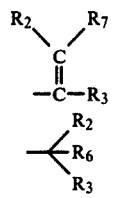 Formula C $R_2$ and $R_3$ are hydrogen, $C_1$ to $C_4$ alkyl or $C_1$ to $C_4$ alkoxy, or hydroxymethyl;

$R_4$ and $R_5$ are $C_1$ to $C_4$ alkyl;

$R_6$ is hydrogen, an ester derivative of hydroxy, hydroxy, benzoyloxy, or halide;

and $R_7$ is hydroxyl, hydrogen, $C_1$ to $C_4$ alkyl or $C_1$ to $C_4$ alkoxy.

2. The $\beta$-lactam of claim 1 wherein Z is

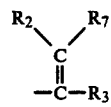

3. The $\beta$-lactam of claim 1 wherein Z is

4. The $\beta$-lactam of claim 1 wherein Z is

* * * * *